US011350878B2

(12) United States Patent
Nam et al.

(10) Patent No.: US 11,350,878 B2
(45) Date of Patent: Jun. 7, 2022

(54) APPARATUS AND METHOD FOR ESTIMATING BIO-INFORMATION

(71) Applicant: SAMSUNG ELECTRONICS CO., LTD., Suwon-si (KR)

(72) Inventors: Jung Yong Nam, Hwaseong-si (KR); Kak Namkoong, Seoul (KR); Yeol Ho Lee, Anyang-si (KR); Joon Hyung Lee, Seongnam-si (KR); Ki Young Chang, Seoul (KR); Won Jong Jung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 351 days.

(21) Appl. No.: 16/574,937

(22) Filed: Sep. 18, 2019

(65) Prior Publication Data
US 2020/0253558 A1 Aug. 13, 2020

(30) Foreign Application Priority Data

Feb. 7, 2019 (KR) .................. 10-2019-0014555

(51) Int. Cl.
*A61B 5/00* (2006.01)
*A61B 5/145* (2006.01)
(Continued)

(52) U.S. Cl.
CPC .......... *A61B 5/7203* (2013.01); *A61B 5/0008* (2013.01); *A61B 5/01* (2013.01);
(Continued)

(58) Field of Classification Search
CPC . A61B 5/7203; A61B 5/14532; A61B 5/1455; A61B 5/01; A61B 5/0008;
(Continued)

(56) References Cited

U.S. PATENT DOCUMENTS 6,289,230 B1 9/2001 Chaiken et al.
7,884,933 B1 * 2/2011 Kashyap ............. G01N 21/474
356/338

(Continued)

FOREIGN PATENT DOCUMENTS

JP 2008-237775 A 10/2008
KR 10-2017-0035675 A 3/2017
(Continued)

OTHER PUBLICATIONS

Tamara L. Troy et al., "Optical properties of human skin in the near infrared wavelength range of 1000 to 2200 nm", Journal of Biomedical Optics, vol. 6, No. 2, SPIE, Apr. 2001, pp. 167-176.
(Continued)

*Primary Examiner* — Brian T Gedeon
*Assistant Examiner* — Joshua Andrew Schum-Houck
(74) *Attorney, Agent, or Firm* — Sughrue Mion, PLLC

(57) ABSTRACT

An apparatus for estimating bio-information may include a sensor configured to emit light to an object and detect light scattered or reflected from the object and a processor configured to acquire, based on an intensity of the detected light, a first absorbance coefficient change and a first scattering coefficient change, relative to a reference time point, acquire a second scattering coefficient change based on the first absorbance coefficient change, and correct the first scattering coefficient change based on the acquired second scattering coefficient change.

19 Claims, 6 Drawing Sheets

(51) Int. Cl.
*A61B 5/1455* (2006.01)
*A61B 5/01* (2006.01)
(52) U.S. Cl.
CPC ........ *A61B 5/1455* (2013.01); *A61B 5/14532* (2013.01); *A61B 5/14546* (2013.01); *A61B 5/681* (2013.01)
(58) Field of Classification Search
CPC ... A61B 5/14546; A61B 5/681; A61B 5/0075; A61B 5/7235; A61B 5/7275
See application file for complete search history.

(56) References Cited

U.S. PATENT DOCUMENTS

| | | | |
|---|---|---|---|
| 10,188,328 B2 | 1/2019 | Shimizu et al. | |
| 2005/0043597 A1 | 2/2005 | Xie | |
| 2005/0154277 A1 | 7/2005 | Tang et al. | |
| 2007/0038041 A1* | 2/2007 | Yang | G01N 21/49 600/310 |
| 2011/0136249 A1 | 6/2011 | Stiene | |
| 2015/0148636 A1* | 5/2015 | Benaron | A61B 5/02405 600/328 |
| 2015/0313516 A1* | 11/2015 | Shimizu | A61B 5/14546 600/322 |
| 2015/0369725 A1 | 12/2015 | Carvalho Sousa et al. | |
| 2016/0299007 A1 | 10/2016 | Kleczewski | |
| 2017/0079565 A1 | 3/2017 | Choi et al. | |
| 2017/0319185 A1 | 11/2017 | Choi et al. | |
| 2018/0042583 A1 | 2/2018 | Pringle et al. | |
| 2019/0110720 A1 | 4/2019 | Shimizu et al. | |

FOREIGN PATENT DOCUMENTS

| | | |
|---|---|---|
| KR | 10-2017-0126310 A | 11/2017 |
| WO | 2014/087825 A1 | 6/2014 |

OTHER PUBLICATIONS

Andrea J.R. Balthasar et al., "Optical Signature of Nerve Tissue-Exploratory Ex Vivo Study Comparing Optical, Histological, and Molecular Characteristics of Different Adipose and Nerve Tissues", Lasers in Surgery and Medicine, vol. 50, Wiley Periodicals, Inc., 2018, pp. 948-960.

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2019-0014555, filed on Feb. 7, 2019, in the Korean Intellectual Property Office, the entire disclosure of which is incorporated herein by reference for all purposes.

BACKGROUND

1. Field

Example embodiments of the present disclosure relate to an apparatus and a method for non-invasively estimating bio-information.

2. Description of Related Art

Generally, as a non-invasive method of measuring (or estimating or predicting) bio-information such as, for example, triglycerides, a device including a light source and an optical sensor is placed on a blood vessel and a scattered light signal passing through blood is measured to estimate a concentration of blood triglycerides. Change in concentration of blood triglycerides may appear as change in scattering coefficient of blood, and thus a scattering coefficient change is acquired from a change of a scattered light signal and the concentration of blood triglycerides is estimated. In order to accurately estimate the concentration of blood triglycerides through the change of a scattered light signal, only the scattering coefficient change of blood should induce the change of the scattered light signal. However, in the real implementation, in addition to the scattering coefficient change of blood, various noise factors, such as physical/chemical changes of skin, hemodynamic changes, and the like, may affect the scattered light signal. Also, the scattering coefficient of blood may be changed by other blood substances, in addition to the blood triglycerides, and hence accuracy may be degraded.

SUMMARY

One or more example embodiments provide an apparatus and a method for estimating bio-information in a non-invasive manner with high accuracy.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, an apparatus for estimating bio-information includes a sensor configured to emit light to an object and detect light scattered or reflected from the object and a processor configured to acquire, based on an intensity of the detected light, a first absorbance coefficient change and a first scattering coefficient change, relative to a reference time point, acquire a second scattering coefficient change based on the first absorbance coefficient change, and correct the first scattering coefficient change based on the acquired second scattering coefficient change.

The processor may acquire a second absorbance coefficient change based on the first absorbance coefficient change and acquire the second scattering coefficient change using a relation equation between the second absorbance coefficient change and the second scattering coefficient change.

The processor may acquire the first absorbance coefficient change or a value obtained by reducing the first absorbance coefficient change by a predetermined ratio as the second absorbance coefficient change.

The predetermined ratio may be a preset fixed value or a value adaptively adjusted based on at least one of a characteristic of each user or a type of bio-information to be estimated.

The relation equation may be defined based on two blood samples, a change in bio-information-related component between the two blood samples being less than or equal to a predetermined reference.

The second scattering coefficient change may indicate a scattering coefficient change due to a noise component other than a bio-information-related component.

The processor may estimate bio-information using the corrected first scattering coefficient change and a bio-information estimation model.

The bio-information may include at least one of blood sugar, cholesterol, triglycerides (TG), skin temperature, protein, and uric acid.

The sensor may include a light source configured to emit light to the object of interest and a detector configured to detect light scattered or reflected from the object of interest irradiated by the light source, convert a detected optical signal into an electrical signal, and output the electrical signal.

The light source may include at least one of a light emitting diode (LED) and a laser diode and the detector includes at least one of a photodiode, an image sensor, and a phototransistor.

The apparatus may further include an output interface configured to output a processing result of the processor.

The apparatus may further include a communication interface configured to transmit a processing result of the processor to an external device.

According to an aspect of another example embodiment, a method of estimating bio-information includes emitting light to an object; detecting light scattered or reflected from the object; acquiring, based on an intensity of the detected light, a first absorbance coefficient change and a first scattering coefficient change, relative to a reference time point; acquiring a second scattering coefficient change based on the first absorbance coefficient change; and correcting the first scattering coefficient change based on the second scattering coefficient change.

The acquiring of the second scattering coefficient change may include acquiring a second absorbance coefficient change based on the first absorbance coefficient change and acquiring the second scattering coefficient change using a relation equation between the second absorbance coefficient change and the second scattering coefficient change.

The acquiring of the second absorbance coefficient change may include acquiring the first absorbance coefficient change or a value obtained by reducing the first absorbance coefficient change by a predetermined ratio as the second absorbance coefficient change.

The predetermined ratio may be a preset fixed value or a value adaptively adjusted based on at least one of a characteristic of each user or a type of bio-information to be estimated.

The relation equation may be defined based on two blood samples, a change in bio-information-related component between the two blood samples being less than or equal to a predetermined reference.

The second scattering coefficient change may indicate a scattering coefficient change due to a noise component other than a bio-information-related component.

The method may further include estimating bio-information using the corrected first scattering coefficient change and a bio-information estimation model.

The method may further include outputting a result of estimating bio-information.

Other features and aspects will be apparent from the following detailed description, the drawings, and the claims.

BRIEF DESCRIPTION OF THE DRAWINGS

The above and/or other aspects will become apparent and more readily appreciated from the following description of example embodiments, taken in conjunction with the accompanying drawings in which.

DETAILED DESCRIPTION

Figure 1:
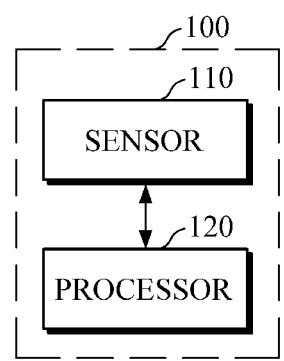
FIG. 1 is a block diagram illustrating an apparatus for estimating bio-information according to an example embodiment.

The following detailed description is provided to assist the reader in gaining a comprehensive understanding of methods, apparatuses and/or systems according to example embodiments. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail.

Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms "first," "second," etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising" will be understood to imply the inclusion of stated elements but not the exclusion of any other elements. Terms such as "unit" and "module" denote units that process at least one function or operation, and they may be implemented by using hardware, software, or a combination of hardware and software.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, embodiments of an apparatus and a method for estimating bio-information will be described in detail with reference to the accompanying drawings.

Figure 2:
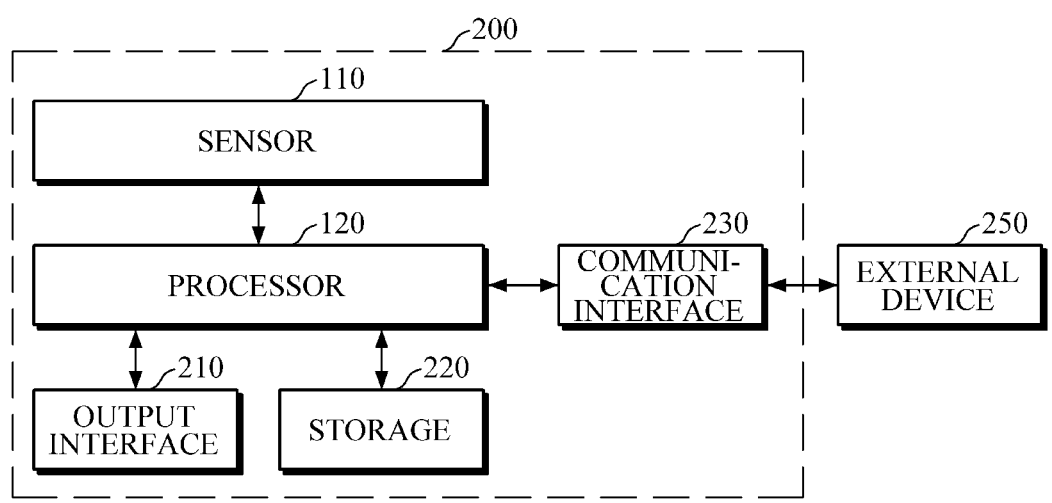
FIG. 2 is a block diagram illustrating an apparatus for estimating bio-information according to another example embodiment.
Figure 3:
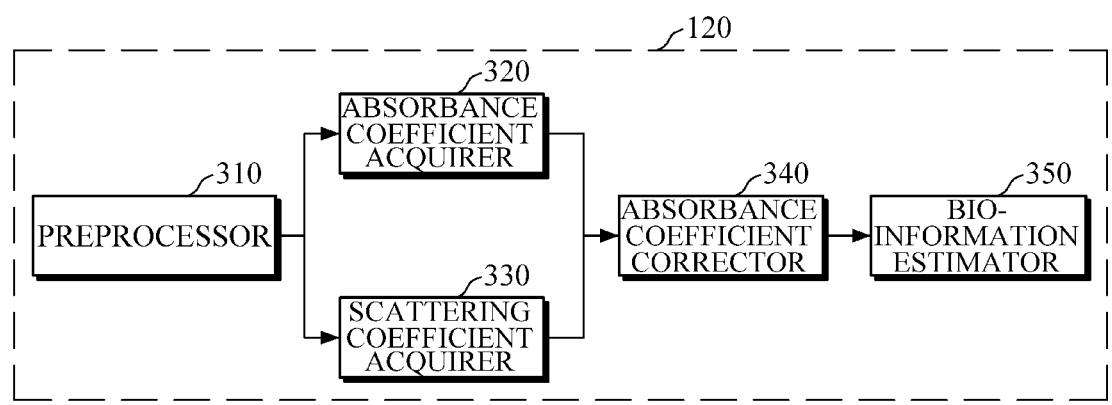
FIG. 3 is a block diagram illustrating an example embodiment of a processor of the apparatus of FIG. 1 and/or the apparatus of FIG. 2.
Figure 4:
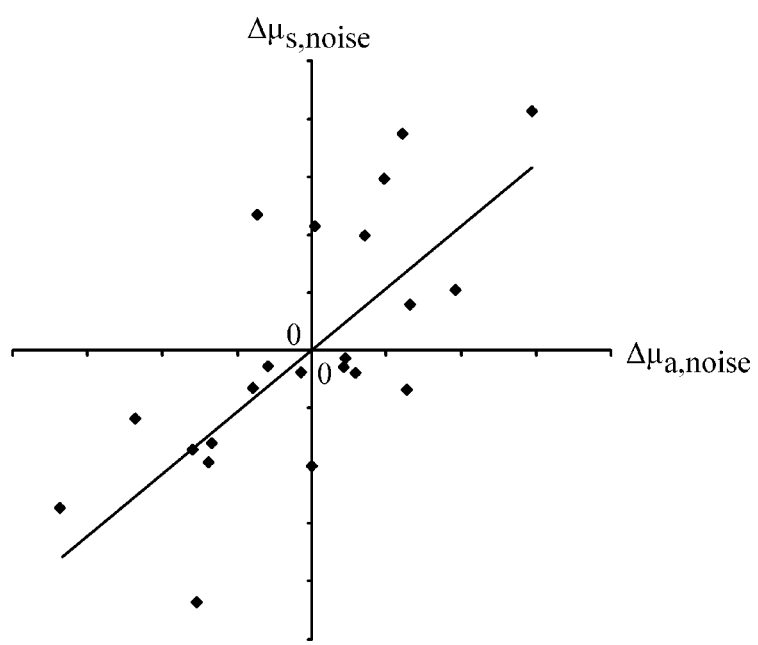
FIG. 4 is a graph for describing a relation equation between a scattering coefficient change due to noise and an absorption coefficient change due to noise.

FIG. 1 is a block diagram illustrating an apparatus for estimating bio-information according to an example embodiment. FIG. 2 is a block diagram illustrating an apparatus for estimating bio-information according to another example embodiment. FIG. 3 is a block diagram illustrating an example embodiment of a processor of the apparatus of FIG. 1 and/or the apparatus of FIG. 2. FIG. 4 is a graph for describing a relation equation between a scattering coefficient change due to noise and an absorption coefficient change due to noise.

Referring to FIGS. 1 and 2, an apparatus 100 for estimating bio-information and an apparatus 200 for estimating bio-information include a sensor 110 and a processor 120.

The sensor 110 may include a light source configured to emit light to an object and a detector configured to detect light scattered or reflected from the object.

The light source may include, for example but not limited to, a light emitting diode (LED), a laser diode (LD), and/or a phosphor. The light source may be formed as a plurality of light source arrays and the plurality of light source arrays may be sequentially driven in a time division manner according to the control of the processor 120. The plurality of light source arrays may be configured to emit light of the same wavelength or light of different wavelengths from each other. For example, the light source may be configured to emit light in a wavelength band of 800 nm for triglyceride measurement (or estimation or prediction). However, an example embodiment is not limited thereto and the light source may be configured to emit light in a different wavelength band according to the type of bio-information, characteristics of an object, characteristics of a user, and the like.

The detector may detect light reflected or scattered from the irradiated object. The detector may convert a detected optical signal into an electrical signal and output the electrical signal. In this case, the electrical signal may be an electrical current signal. The detector may include, for example, a photodiode, a phototransistor (PTr), and/or an image sensor, but is not limited thereto. The detector may be formed as an array of a plurality of detectors and each detector may be disposed at a different distance from the light source.

The processor 120 may acquire a scattering coefficient change for bio-information estimation based on the intensity of light detected by the sensor 110 and estimate bio-information based on the acquired scattering coefficient change. In this case, the scattering coefficient indicates a value by which the intensity of light is reduced due to scattering when light emitted by the light source travels a unit length. For example, the processor 120 may calculate the scattering coefficient by taking into consideration the intensity of detected light, a distance between the light source and the detector, and/or the intensity of light emitted by the light source.

The bio-information may include blood sugar, cholesterol, triglycerides (TG), skin temperature, protein, uric acid, and the like, but is not limited thereto. Hereinafter, a description will be given, mainly focusing on triglycerides for convenience of description.

Generally, in estimation of triglycerides, since a change in scattering coefficient of blood may occur due to blood substances other than triglycerides, the accuracy of estimating triglycerides may be reduced when the scattering coefficient change is used for estimation. Thus, the processor 120 may correct the scattering coefficient change for bio-information estimation based on the absorbance coefficient change, as will be described with reference to FIG. 3. Accordingly, the accuracy of estimating bio-information may be increased.

Referring to FIG. 3, the processor 120 may include a preprocessor 310, an absorbance coefficient acquirer 320, a scattering coefficient acquirer 330, a scattering coefficient corrector 340, and a bio-information estimator 350.

The preprocessor 310 may preprocess a signal received from the sensor 110. For example, when an electrical signal is received from the sensor 110, the preprocessor 310 may amplify the electrical signal or convert the electrical analog signal into a digital signal. In addition, the preprocessor 310 may perform preprocessing, such as noise removal through a filter, normalization, smoothing, or the like.

When a plurality of optical signals are detected, the preprocessor 310 may determine one optical signal to be used in estimating bio-information from among the plurality of optical signals. For example, the preprocessor 310 may select an optical signal having the highest light intensity or determine an optical signal by combining a plurality of optical signals having a light intensity greater than or equal to a threshold level or all of the plurality of optical signals. Alternatively, the preprocessing 310 may determine an optical signal for bio-information estimation by calculating a degree of similarity between two optical signals and combining the optical signals of which a degree of similarity is greater than or equal to a threshold. The criteria for determining the optical signal to be used in bio-information estimation may be preset and are not limited to the above examples. Here, the degree of similarity may include at least one of Euclidean distance, the Pearson correlation coefficient, the Spearman correlation coefficient, and cosine similarity.

The absorbance coefficient acquirer 320 may acquire an absorbance coefficient change relative to a reference time point based on the intensity of light detected by the sensor 110, for example, the intensity of a preprocessed electrical signal. In this case, the reference time point may be an arbitrary point in time before a current bio-information measurement time point and may be a calibration time point. The reference time point may include a point in time when the user is fasting.

For example, the absorbance coefficient at each point in time may be acquired by Equation 1 below. However, an example embodiment is not limited thereto.

$$\ln\left\{\rho^2 \frac{R(\rho)}{S_0}\right\} = -\mu_{eff}\rho + \ln\frac{3\mu_a}{2\pi\mu_{eff}} \quad (1)$$

Here, R(ρ) represents the intensity of light detected by a detector, and ρ represents a distance between the light source and the detector. $\mu_a$ represents an absorbance coefficient, $\mu_{eff}$ represents an effective attenuation coefficient, and $S_0$ represents the intensity of light emitted by the light source.

As such, when the absorbance coefficient is acquired at each of the reference time point and an estimation time point, an absorbance coefficient change may be acquired by subtracting the absorbance coefficient obtained at the reference time point from the absorbance coefficient obtained at the time of estimation. Equation 2 below exemplifies an absorbance coefficient change for estimating triglycerides.

$$\Delta\mu_a = \Delta\mu_{a,TG} + \Delta\mu_{a,noise} \quad 2)$$

Here, $\Delta\mu_a$ represents an absorbance coefficient change. $\Delta\mu_{a,TG}$ represents an absorbance coefficient change due to triglycerides and $\Delta\mu_{a,noise}$ represents an absorbance coefficient change due to noise other than triglycerides.

When the absorbance coefficient acquirer 320 may acquire the absorbance coefficient change (hereinafter referred to as a "first absorbance coefficient change") using the light intensity detected by the sensor 110 and acquire an absorbance coefficient change (hereinafter referred to as a "second absorbance coefficient change") due to noise other than a bio-information-related component based on the first absorbance coefficient change.

For example, the absorbance coefficient acquirer 320 may acquire the first absorbance coefficient change itself as the second absorbance coefficient change by assuming that the absorbance coefficient change due to the bio-information-related component is zero. Alternatively, a value obtained by reducing the first absorbance coefficient change by a predetermined ratio may be acquired as the second absorbance coefficient change. In this case, the predetermined ratio may be a fixed value obtained by preprocessing process. Alternatively, the predetermined ratio may be a value adaptively adjusted by taking into consideration a user characteristic, such as the sex, age, or health condition of the user, or the type of bio-information to be estimated.

The scattering coefficient acquirer 330 may acquire a scattering coefficient change relative to the reference time point based on the light intensity detected by the sensor 110. In this case, the reference time point is an arbitrary point in time before a time for estimating a bio-information (or a bio-information estimation time point). For example, the reference time point may be a calibration time point, and include a point in time when the user is fasting.

For example, the scattering coefficient at each point in time may be acquired by using Equation 3 below.

$$\ln\left\{\rho^3 \frac{R(\rho)}{S_0}\right\} = -\mu_{eff}\rho + \ln\frac{1}{2\pi\mu'_s} \quad (3)$$

Here, R(ρ) represents the intensity of light detected by a detector, and ρ represents a distance between the light source and the detector. $\mu_s$ represents a scattering coefficient, $\mu_{eff}$ represents an effective attenuation coefficient, and $S_0$ represents the intensity of light emitted by the light source.

In another example, when there are a plurality of detectors, the scattering coefficient may be calculated by using Equation 4 below.

$$\mu'_s = \frac{1}{3\mu_s}\left\{\frac{1}{\rho_2 - \rho_1}\ln\frac{\rho_1^2 R(\rho_1)}{\rho_1^2 R(\rho_2)}\right\}^2 \quad (4)$$

Here, $\rho_1$ represents a distance between the light source and a first detector and $\rho_2$ represents a distance between the light source and a second detector. $R(\rho_1)$ represents the intensity of light detected by the first detector and $R(\rho_2)$ represents the intensity of light detected by the second detector. $\mu_s$ represents a scattering coefficient. Thus, a scattering coefficient calculation formula may be differently defined according to the number of detectors that detect light emitted by the light source.

When the scattering coefficient is acquired at each of the reference time point and the bio-information estimation time point, the scattering coefficient acquirer 330 may acquire a scattering coefficient change by subtracting the scattering coefficient acquired at the reference time point from the scattering coefficient acquired at the time of estimation. Equation 5 below exemplifies a scattering coefficient change for estimating triglycerides.

$$\Delta\mu_s = \Delta\mu_{s,TG} + \Delta\mu_{s,noise} \qquad (5)$$

Here, $\Delta\mu_s$ represents a scattering coefficient change. $\Delta\mu_{s,TG}$ represents a change in scattering coefficient due to triglycerides and $\Delta\mu_{s,noise}$ represents a change in scattering coefficient due to noise other than triglycerides.

When the scattering coefficient change (hereinafter referred to as a "first scattering coefficient change") is acquired based on the light intensity detected by the sensor 110, the scattering coefficient acquirer 330 may acquire a scattering coefficient change (hereinafter referred to as a "second scattering coefficient change") due to noise other than a bio-information-related component based on the acquired second absorbance coefficient change acquired by the absorbance coefficient acquirer 320. For example, when the second absorbance coefficient change is acquired, the scattering coefficient acquirer 330 may acquire the second scattering coefficient change using a relation equation representing a correlation between the second absorbance coefficient change and the second scattering coefficient change.

The relation equation between the second absorbance coefficient change and the second scattering coefficient change may be defined using two blood samples in which the change in bio-information-related component is less than or equal to a predetermined reference value. In this case, the two blood samples may be collected from a plurality of users using an invasive method. Alternatively, a plurality of blood samples may be collected from a specific user using an invasive method. In this case, the predetermined reference value may be set differently according to the type of bio-information, characteristics of the user, or the like. However, an example embodiment is not limited thereto, and it is possible to derive a relation equation using two or more sample solutions which are composed similarly to human blood by varying the amount of noise component except for bio-information-related component.

For example, two blood samples with the same triglycerides or triglycerides having little difference and thus having a triglyceride change lower than or equal to a predetermined reference (e.g., 3 mg/dL) are used to acquire the change in absorbance coefficient and the change in scattering coefficient between the two blood samples. In this case, the obtained absorbance coefficient change and scattering coefficient change may be considered as the second absorbance coefficient change and the second scattering coefficient change due to noise, respectively. To satisfy such a reference, second absorbance coefficient change data and the second scattering coefficient change data are obtained multiple times and the obtained data may be displayed on a graph as shown in FIG. 4, thereby deriving a linear relation equation between the second absorbance coefficient change and the second scattering coefficient change as shown in Equation 6. However, an example embodiment is not particularly limited to the linear relation equation, and a linear/nonlinear relation equation may be defined using various methods, such as linear/nonlinear regression analysis, neural network, deep learning, and the like.

$$y = ax + b \qquad (6)$$

Here, y represents a second scattering coefficient change and x represents a second absorbance coefficient change. a and b are coefficients acquired by the above process.

When the second scattering coefficient change is acquired, the scattering coefficient corrector 340 may correct the first scattering coefficient change using the acquired second scattering coefficient change. For example, the scattering coefficient change due to a bio-information-related component may be acquired by subtracting the second scattering coefficient change from the first scattering coefficient change using Equation 5.

The bio-information estimator 350 may estimate bio-information using the corrected first scattering coefficient change. For example, the bio-information estimator 350 may estimate the bio-information by applying a bio-information estimation model to the corrected first scattering coefficient. In this case, the bio-information estimation model may be given in the form of a linear/nonlinear function or matching table that represents a correlation between scattering coefficients and estimated bio-information values.

The bio-information estimation model may be a model used to acquire an amount of change in bio-information relative to a reference time point based on the change in the first scattering coefficient relative to the reference time point. In this case, when the amount of change in bio-information at the time of estimation is obtained, an estimated bio-information value at the time of estimation may be acquired using a bio-information value at the reference time point as an offset. Equation 7 below is an example of a triglyceride calculation formula.

$$TG_{est} = \Delta TG_{est} + TG_{cal} \qquad (7)$$

Here, $TG_{est}$ represents an estimated triglyceride value, $\Delta TG_{est}$ represents the amount of change in triglyceride at the time of estimation, and $TG_{cal}$ represents a triglyceride value at the reference time point.

Referring back to FIG. 2, the apparatus 200 for estimating bio-information may further include an output interface 210, a storage 220, and a communication interface 230.

The output interface 210 may output a processing result of the processor 120 to be provided to the user. For example, the output interface 210 may provide the processing result to the user using various visual/non-visual methods, such as a visual output module, such as a display, an audio output module, such as a speaker, a haptic module which provides information using vibration or tactile sensation, and the like. In addition, when the triglyceride value is out of a preset range, the output interface 210 may output warning information. In this case, the warning information may be provided to the user by using a visual indicator, such as changing the color of the triglyceride value output to the display, or using any other form such as, for example, a tactile or vibration method through a haptic module.

A variety of reference information to be used for estimating bio-information or the processing result of the processor 120 may be stored in the storage 220. For example, the reference information may include a light source driving condition, a relation equation between the second absorbance coefficient change and the second scattering coefficient change, information related to a bio-information estimation model, user information, such as the age, sex, and health status of the user, and the like.

The storage 220 may include a storage medium of at least one type of flash memory type, hard disk type, multimedia card micro type, card-type memory (e.g., secure digital (SD) or extreme digital (XD) memory), random access memory (RAM), static random access memory (SRAM), read only memory (ROM), electrically erasable programmable read only memory (EEPROM), programmable read only memory (PROM), magnetic memory, magnetic disk, optical disk, and the like, but is not limited thereto.

The communication interface 230 may transmit and receive a variety of information for estimating bio-information by communicating with an external device 250. For example, the external device 250 may be a medical-related device that establishes a relation equation between the second absorbance coefficient change and the second scattering coefficient change for various users, a bio-information estimation model, and the like. In addition, the external device 250 may receive the processing result of the processor 120 and provide the same to the user, and may include an information processing device, for example, a smartphone, a tablet personal computer (PC), a desktop PC, a notebook PC, and the like.

The communication interface 230 may utilize communication technologies, such as Bluetooth, Bluetooth low energy (BLE), near field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, RFID communication, 3G communication, 4G communication, 5G communication. However, the communication technologies are not limited to the above examples.

Figure 5:
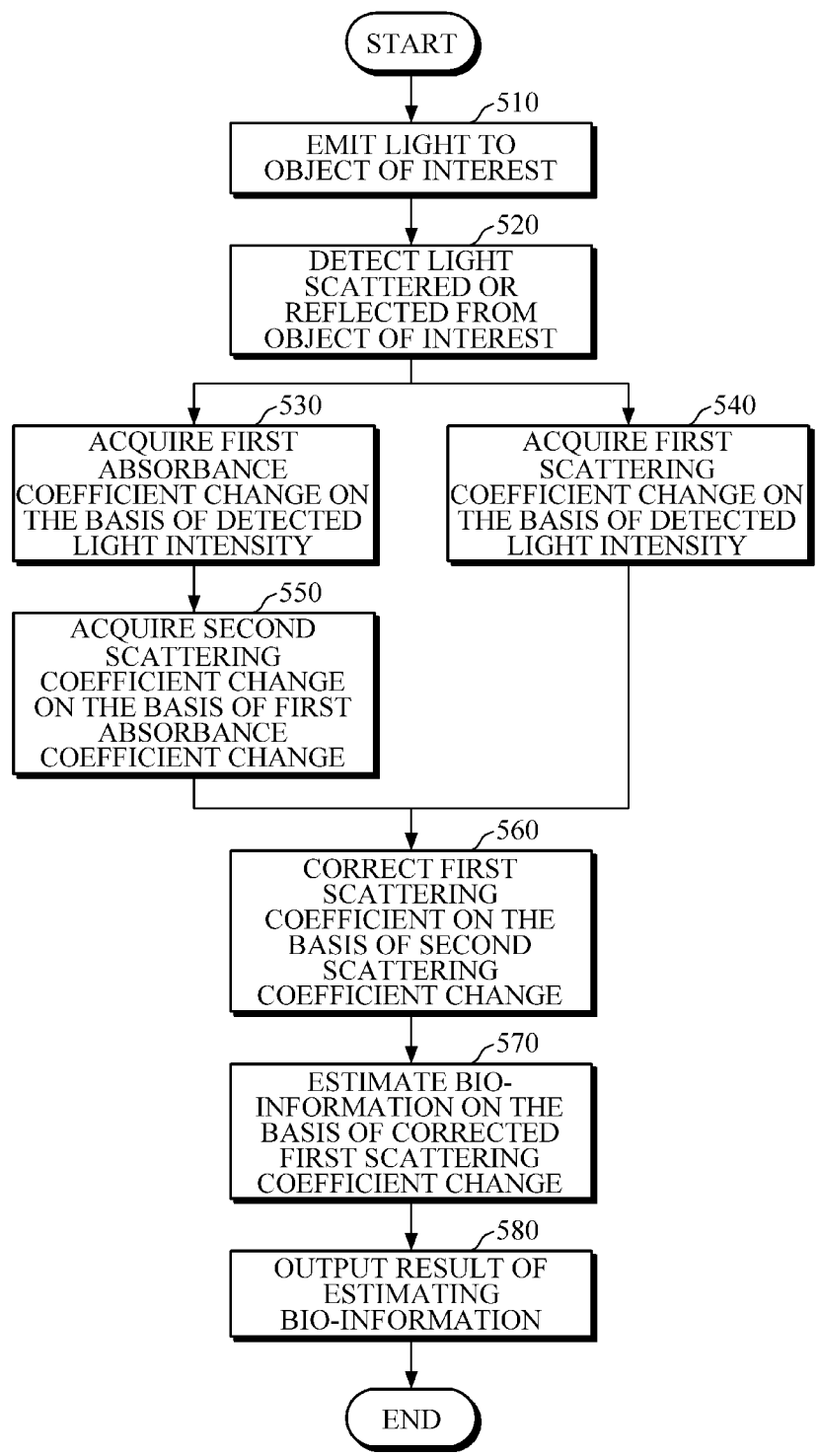
FIG. 5 is a flowchart illustrating a method of estimating bio-information according to an example embodiment.

FIG. 5 is a flowchart illustrating a method of estimating bio-information according to an example embodiment.

The method of FIG. 5 is an example embodiment of a method of estimating bio-information performed by the apparatus 100 of FIG. 1 and/or the apparatus 200 of FIG. 2.

The apparatus 100 and/or apparatus 200 for estimating bio-information may emit light to an object by driving a light source upon request for estimation of bio-information (510). The request for estimation of bio-information may be input by a user or an external device. Alternatively, when the bio-information is continuously estimated, the request may be automatically issued at a preset estimation interval. In addition, the light source may include an LED, a laser diode, and the like. The light source may be formed as a plurality of arrays and each light source may be configured to emit light of a different wavelength.

Then, light scattered or reflected from the object may be detected through a detector (520). The detector may include a photodiode, a phototransistor, and/or an image sensor and may be formed as a plurality of arrays. The detector may detect light scattered or reflected from the object, convert the light into an electrical signal, and output the electrical signal.

Then, a first absorbance coefficient change may be acquired based on the intensity of the light detected in operation 520 (530). For example, absorbance coefficients at a reference time point and an estimation time point may be acquired using Equation 1 above and a change in absorbance coefficient between the two time points may be acquired using the acquired absorbance coefficients.

Further, a first scattering coefficient change may be acquired based on the intensity of the light detected in operation 520 (540). For example, scattering coefficients at the reference time point and the estimation time point may be acquired using Equation 3 or 4 above and a change in the scattering coefficients at the two time points may be acquired using the acquired scattering coefficients.

Then, a second scattering coefficient change may be acquired using the first absorbance coefficient change (550). For example, it is assumed that the absorbance coefficient change due to a bio-information-related component is not significantly large in the first absorbance coefficient change between the reference time point and the estimation time point, and the first absorbance coefficient change may be acquired as the second absorbance coefficient change. Alternatively, a value determined by reducing the first absorbance coefficient change by a specific ratio determined by taking into account the user's characteristic or the type of bio-information to be obtained may be acquired as the second absorbance coefficient change.

As described above, when the second absorbance coefficient change is acquired, the second scattering coefficient change may be acquired using a relation equation representing a correlation between the second absorbance coefficient change and the second scattering coefficient change. In this case, the relation equation between the second absorbance coefficient change and the second scattering coefficient change may be derived using two blood samples with little change in a bio-information-related component (e.g., change in triglycerides). That is, when the two blood samples have the same level of triglycerides, the change in absorbance coefficient or the change in scattering coefficient between the two blood samples may be considered to be due to a noise component and thus the relation equation between the second absorbance coefficient change and the second scattering coefficient change may be acquired by regarding the absorbance coefficient change and the scattering coefficient change acquired from the two blood samples as the second absorbance coefficient change and the second scattering coefficient change.

Then, when the second scattering coefficient change is acquired in operation 550, the first scattering coefficient change may be corrected using the second scattering coefficient change (560). For example, a scattering coefficient change due to the bio-information-related component may be acquired by subtracting the second scattering coefficient change from the first scattering coefficient change using Equation 5 above.

Thereafter, bio-information may be estimated using the first scattering coefficient change corrected in operation 560, i.e., the acquired scattering coefficient change due to the bio-information-related component (570). For example, an amount of change in bio-information relative to the reference time point may be acquired by applying a bio-information estimation model to the first scattering coefficient change and the bio-information may be estimated by applying an offset to the acquired amount of change in bio-information. In this case, the offset may be a bio-information value measured at the reference time point.

Then, a result of estimating bio-information may be output and provided to the user (580). For example, the bio-information estimation result may be visually output using a display module or output in a non-visual manner, such as voice, vibration, or tactile sensation, using a speaker module or a haptic module.

Figure 6:
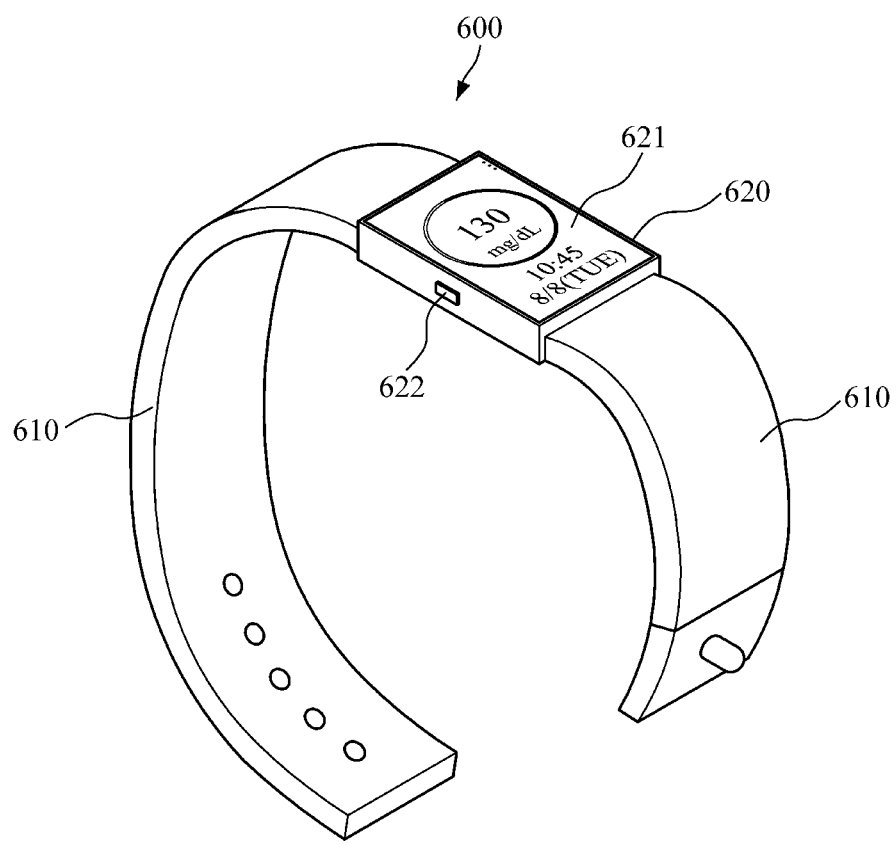
FIG. 6 is a diagram illustrating a wearable device according to an example embodiment.

FIG. 6 is a diagram illustrating a wearable device according to an example embodiment. FIG. 6 illustrates a smart watch or smart band-type wearable device in which the above-described apparatus 100 and/or 200 for estimating bio-information is mounted.

Referring to FIG. 6, the wearable device 600 may include a strap 610 and a main body 620 to which the strap is connected. A battery for supplying power to the wearable device 600 may be embedded in the strap 610 or the main body 600.

The strap 610 may be flexibly formed to be wrapped around a wrist of a user, thereby allowing the main body to be fixed onto the wrist, and may be configured separately as shown in FIG. 6 or may be configured integrally.

Configurations of the apparatus 100 and/or 200 for estimating bio-information and configurations for performing other functions may be mounted in the main body 620.

A sensor configured to emit light to the skin of the wrist when the wrist of the user makes contact with a rear surface of the main body 620 and to detect light scattered or reflected from living tissue, such as the skin or blood vessel of the wrist, may be mounted on the rear surface. The sensor may be formed as a plurality of light source arrays or a plurality of detector arrays, and each light source may emit light of the same wavelength or a different wavelength. The light source may include an LED and/or a laser diode and the detector may include a photodiode, an image sensor, and/or a phototransistor.

An image capturer configured to acquire an image may be mounted on the rear surface of the main body 620. The image capturer may acquire an image of a wrist for guiding a contact state when the wrist is in contact with the rear surface of the main body 620.

A processor for processing various functions for estimating bio-information and other functions may be mounted in the main body 620. For example, the processor may be electrically connected to the sensor and control the sensor or receive an optical signal measured by the sensor upon request of the user to estimate bio-information.

The processor may estimate bio-information using the received optical signal. For example, the processor may acquire an absorbance coefficient change or a scattering coefficient change based on the intensity of the optical signal, and acquire a scattering coefficient change due to a component related to bio-information of interest by correcting the acquired scattering coefficient change using the acquired absorbance coefficient change. According to an example embodiment, it is possible to increase the accuracy by estimating bio-information using the acquired scattering coefficient change due to the bio-information-related component.

In addition, a display 621 may be mounted on a front surface of the main body 620. The display 621 may include a touch screen which allows a touch input of the user. The display 621 may receive the touch input of the user and transmit the touch input to the processor. In addition, the display 621 may visually output a processing result of the processor to provide it to the user.

Also, an operator 622 that enables the user to input various commands may be mounted on one side of the main body 620. The operator 622 may transmit the command input by the user to the processor. The operator 622 may include a function to turn on/off the wearable device 600.

Example embodiments may be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner. Also, functional programs, codes, and code segments for accomplishing the present disclosure can be easily construed by programmers skilled in the art to which the present disclosure pertains.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in some of block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating bio-information, the apparatus comprising:
 a sensor configured to emit light to an object and detect light scattered or reflected from the object; and
 a processor configured to:
  acquire, based on an intensity of the detected light, a first absorbance coefficient change and a first scattering coefficient change, relative to a reference time point,
  acquire a second scattering coefficient change based on the first absorbance coefficient change, and correct the first scattering coefficient change based on the acquired second scattering coefficient change, wherein the processor is further configured to acquire a second absorbance coefficient change based on the first absorbance coefficient change, and acquire the second scattering coefficient change based on a relation equation that is preset between the second absorbance coefficient change and the second scattering coefficient change, and wherein the processor is further configured to acquire, from two blood samples, a plurality of sets of an absorbance coefficient change and a scattering coefficient change, and derive the relation equation from the plurality of sets.

2. The apparatus of claim 1, wherein the processor is further configured to acquire the first absorbance coefficient change or a value obtained by reducing the first absorbance coefficient change by a predetermined ratio as the second absorbance coefficient change.

3. The apparatus of claim 2, wherein the predetermined ratio is a preset fixed value or a value adaptively adjusted based on at least one of a characteristic of each user or a type of bio-information to be estimated.

4. The apparatus of claim 1, wherein a change in bio-information-related component between the two blood samples is less than or equal to a predetermined reference.

5. The apparatus of claim 1, wherein the second scattering coefficient change indicates a scattering coefficient change due to a noise component other than a bio-information-related component.

6. The apparatus of claim 1, wherein the processor is further configured to estimate bio-information based on the corrected first scattering coefficient change and a bio-information estimation model.

7. The apparatus of claim 6, wherein the bio-information comprises at least one of blood sugar, cholesterol, triglycerides (TG), skin temperature, protein, and uric acid.

8. The apparatus of claim 1, wherein the sensor comprises:
a light source configured to emit light to the object; and
a detector configured to detect light scattered or reflected from the object irradiated by the light source, convert a detected optical signal into an electrical signal, and output the electrical signal.

9. The apparatus of claim 8, wherein the light source comprises at least one of a light emitting diode and a laser diode, and the detector comprises at least one of a photodiode, an image sensor, and a phototransistor.

10. The apparatus of claim 1, further comprising an output interface configured to output a processing result of the processor.

11. The apparatus of claim 1, further comprising a communication interface configured to transmit a processing result of the processor to an external device.

12. A method of estimating bio-information, the method comprising:
emitting light to an object;
detecting light scattered or reflected from the object;
acquiring, based on an intensity of the detected light, a first absorbance coefficient change and a first scattering coefficient change, relative to a reference time point;
acquiring a second scattering coefficient change based on the first absorbance coefficient change; and
correcting the first scattering coefficient change based on the second scattering coefficient change, wherein the acquiring the second scattering coefficient change comprises acquiring a second absorbance coefficient change based on the first absorbance coefficient change, and acquire the second scattering coefficient change based on a relation equation that is preset between the second absorbance coefficient change and the second scattering coefficient change, and wherein the relation equation is obtained by acquiring, from two blood samples, a plurality of sets of an absorbance coefficient change and a scattering coefficient change, and deriving the relation equation from the plurality of sets.

13. The method of claim 12, wherein the acquiring of the second absorbance coefficient change comprises acquiring the first absorbance coefficient change or a value obtained by reducing the first absorbance coefficient change by a predetermined ratio as the second absorbance coefficient change.

14. The method of claim 13, wherein the predetermined ratio is a preset fixed value or a value adaptively adjusted based on at least one of a characteristic of each user or a type of bio-information to be estimated.

15. The method of claim 12, wherein a change in bio-information-related component between the two blood samples is less than or equal to a predetermined reference.

16. The method of claim 12, wherein the second scattering coefficient change indicates a scattering coefficient change due to a noise component other than a bio-information-related component.

17. The method of claim 12, further comprising estimating bio-information based on the corrected first scattering coefficient change and a bio-information estimation model.

18. The method of claim 17, further comprising outputting a result of the estimating the bio-information.

19. The apparatus of claim 1, wherein the processor is further configured to correct the first scattering coefficient change by subtracting the second scattering coefficient change from the first scattering coefficient change.

* * * * *